US00PP16535P2

(12) United States Plant Patent
Trees

(10) Patent No.: US PP16,535 P2
(45) Date of Patent: May 16, 2006

(54) ***LANTANA* PLANT NAMED 'BALUCREHOT'**

(50) Latin Name: *Lantana camara*
Varietal Denomination: Balucrehot

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 114 days.

(21) Appl. No.: 11/022,721

(22) Filed: Dec. 27, 2004

(51) Int. Cl.
*A01H 5/00* (2006.01)

(52) U.S. Cl. ..... Plt./227

(58) Field of Classification Search ..... Plt./227
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Lantana* plant named 'Balucrehot' characterized by its flower color transitioning from yellow when first open to orange-red when fully mature, dark green-colored foliage, and compact, upright, and spreading growth habit.

1 Drawing Sheet

Latin name of genus and species of plant claimed: *Lantana camara.*
Variety denomination: 'Balucrehot'.

BACKGROUND OF THE INVENTION

The present invention relates to a new and distinct cultivar of *Lantana* plant botanically known as *Lantana camara* and hereinafter referred to by the cultivar name 'Balucrehot'.

The new cultivar originated in a controlled breeding program during August 2000 at Arroyo Grande, Calif. The objective of the breeding program was the development of new *Lantana* cultivars with a well-branched and compact growth habit, continuous flowering, and dark green-colored foliage.

The new cultivar was the product of the open-pollination of the commerically available *Lantana* cultivar 'Robpatdes', U.S. Plant Pat. No. 10,156, characterized by its dark red/yellow-colored flowers, and compact and upright growth habit. The new cultivar was discovered and selected by the inventor in December 2000 at Arroyo Grande, Calif. as a single flowering plant within the progeny of the above stated open-pollination.

Asexual reproduction of the new cultivar by terminal stem cuttings since December 2000 at Arroyo Grande, Calif. and West Chicago, Ill. has demonstrated that the new cultivar reproduces true to type with all the characteristics, as herein described, firmly fixed and retained through successive generations of such asexual propagation.

SUMMARY OF THE INVENTION

The following characteristics of the new cultivar have been repeatedly observed and can be used to distinguish 'Balucrehot' as a new and distinct cultivar of *Lantana* plant:

1. Flower color transitioning from yellow when first open to orange-red at maturity.
2. Dark green-colored foliage.
3. Compact, upright, and spreading growth habit.

Of the many commerically available *Lantana* cultivars know to the inventor, the most similar to the new cultivar is 'Robpatdes', U.S. Plant Pat. No. 10,156. However, in side-by-side comparisions, plants of the new cultivar differ from plants of 'Robpatdes' in the following characteristics:

1. Plants of the new cultivar have smaller leaves than plants of 'Robpatdes'.
2. Plants of the new cultivar have fewer flowers per cluster than plants of 'Robpatdes'.
3. The flowers of the new cultivar are different colors than the flowers of 'Robpatdes'.

BRIEF DESCRIPTION OF THE PHOTOGRAPHS

The accompying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balucrehot'. The plants were grown for 7 weeks in a greenhouse at West Chicago, Ill.

DETAILED BOTANICAL DESCRIPTION

Figure 1:
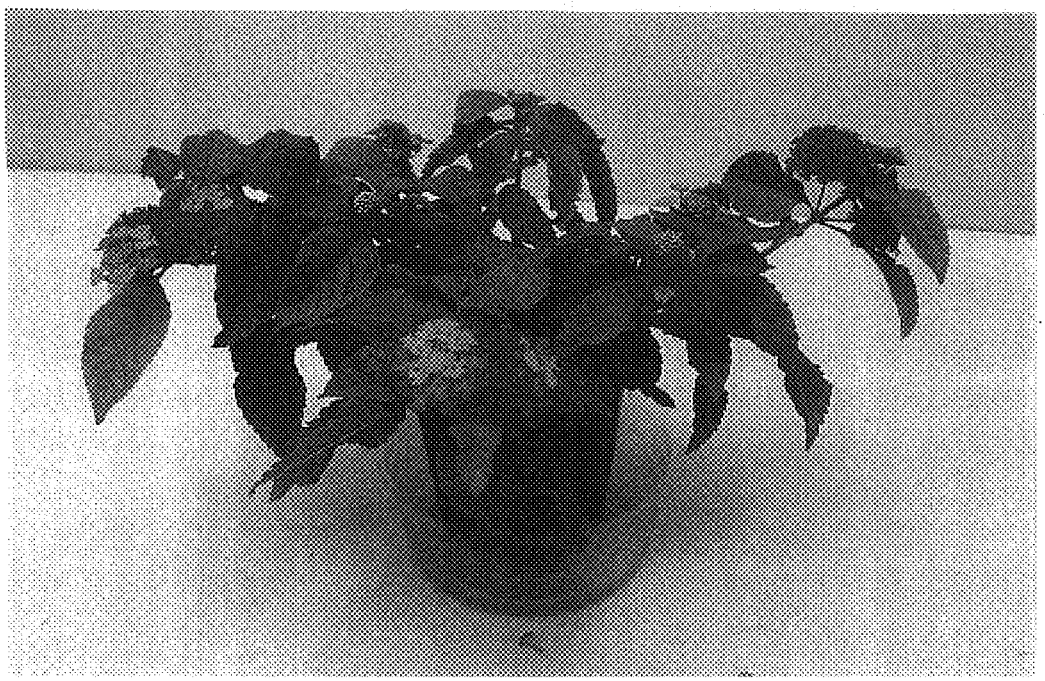
FIG. 1 illustrates a side view of the overall growth and flowering habit of 'Balucrehot'.
Figure 2:
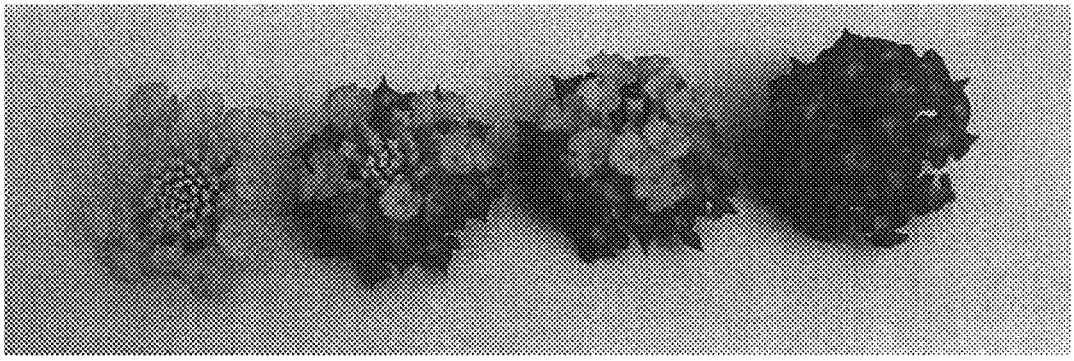
FIG. 2 illustrates a close-up view of a series of inflorescences of 'Balucrehot' showing the transition in coloration from first open (at left) to fully mature (at right).
Figure 3:
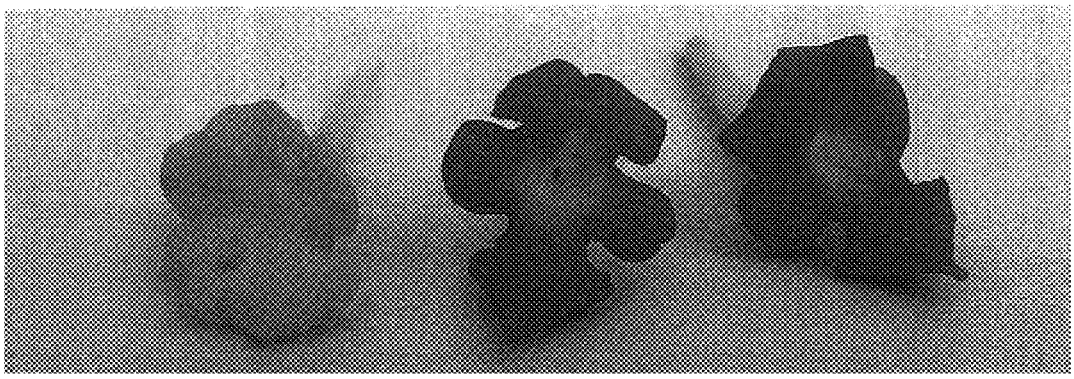
FIG. 3 illustrates a series of individual florets of 'Balucrehot' showing the transition in coloration from first open (at left) to fully mature (at right).

The new cultivar has not been observed under all possible environmental conditions to date. Accordingly, it is possible that the phenotype may vary somewhat with variations in the environment, such as temperature, light intensity, and day length without, however, any variance in genotype.

The chart used in the identification of colors described herein is The R.H.S. Colour Chart of The Royal Horticultural Society, London, England, 2001 edition, except where general color terms of ordinary significance are used. The color values were determined on Sep. 24, 2004 between 9:00 and 11:00 a.m. under natural light conditions.

The following descriptions and measurements describe plants produced from terminal stem cuttings taken from stock plants and grown in a double polycarbonate-covered greenhouse under conditions comparable to those used in commerical practice. The plants were grown at West Chicago, Ill. in 10 cm pots for 7 weeks while utilizing a soilless growth medium. Greenhouse tempatures were maintained at approximately 75°–85 ° F. (24°–29° C.) during the day and approximately 62°–68° F. (17°—20 ° C.) during the night. Greenhouse light levels were maintained at 4,000 to 10,000 footcandles during the day.

Botanical classification: *Lantana camara* cultivar Balucrehot.

Parentage: Open-pollination of 'Robpatdes', U.S. Plant Pat. No. 10,156.

Propagation:

*Type cutting.*—Terminal stem cutting.

*Time to initiate roots.*—Approximately 7 to 11 days.

*Time to produce a rooted cutting.*—Approximately 4 weeks.

*Root description.*—Fine, fibrous.

*Rooting habit.*—Freely branching.

Plant description:

*Crop time.*—Approximately 6–7 weeks from a rooted cutting.

*Form.*—Compact, upright, mounded.

*Growth habit.*—Moderately vigorous forming lateral branches at every node. Pinching enhances basal branching.

*Size.*—Height from soil level to top of plant plane: Approximately 15.5 cm. Diameter (area of spread): Approximately 25.6 cm.

*Main branches.*—Quantity: Approximately 3. Shape: Square in cross section. Strength: Strong. Length: Approxmately 13.3 cm. Diameter: Approximately 2.7 mm. Texture: Hirsute. Color of young supple branch: 144A. Color of mature woody branch: Streaks of 199B and 199C. Internode length at middle of stem: Approximately 2.7 cm.

*Foliage.*—Quantity per lateral branch: Approximately 11. Fragrance: Strong, spicy. Type: Simple. Arrangement: Opposite. Orientation to stem: Obtuse. Shape: Ovate. Margin: Dentate. Apex: Acuminate. Base: Obtuse. Venation pattern: Pinnate. Leaf length: Approximately 5.1 cm. Leaf width: Approximately 3.4 cm. Texture of upper surface: Strigose. Texture of lower surface: Strigose, densely covered with short, stiff hairs. Color of upper surface of mature foliage: Closest to 139A with veins of 151C. Color of lower surface of mature foliage: Slightly darker than 147A with veins closest to but lighter than 146D. Petiole length: Approximately 7 mm. Petiole diameter: Approximately 1.8 mm. Petiole texture of both surface: Strigose. Petiole color of both surfaces: Closest to 146C.

Flowering description:

*Flowering habit.*—Freely flowering under outdoor growing conditions with substantially continuous blooming from spring through autumn and year round in greenhouse environment.

Inflorescence description:

*Type.*—Terminal cluster.

*Shape.*—Spherical.

*Quantity per plant.*—Approximately 4 open at any one time.

*Size.*—Depth (height): Approximately 2.1 cm. Diameter: Approximately 3.8 cm. Number of flowers per inflorescence: Approximately 53 fully opened flowers at any one time. Each flower is subtended by a single bract.

*Bract.*—Shape: Lanceolate. Length: Approximately 3.8 mm. Width: Approximately 1.1 mm. Apex: Cuspidate. Base: Truncate. Margin: Entire. Texture: Lower/outer surface: Densely pubescent. Upper/inner surface: Glabrous. Color of both surfaces: 145C.

*Peduncle.*—Shape: Square in cross section. Length: Approximately 4.2 cm. Diameter: Approximately 1 mm. Angle to stem: 45 degrees. Strength: Strong. Texture: Strigose. Color: Darker than144A.

Flower description:

*Type.*—Salverform.

*Fragrance.*—Light, sweet.

*Aspect.*—Upward, outward.

*Lastingness of fully open bloom.*—Approximately 5–7 days.

*Bud.*—Buds open in progression from the margin to the center of the inflorescence. Shape: Roughly rectangular. Length: Approximately 3.7 mm. Width: Approximately 2.7 mm. Color: 17C.

*Corolla size.*—Length:Approximately 1.1 cm. Width: Approximately 9 cm.

*Petals.*—Quantity: Five. Arrangement: Non imbricate, non-symmetrical, fused at base forming corolla tube. Shape: Obovate. Apex: Obtuse. Texture of upper and lower surfaces: Glabrous. Color when first open: Upper surface: 13A. Lower surface: 13C. Color when fully open: Upper surface: 13A with overlay of 21B. Lower surface: 8A with 23B along margin. Petal color when fully mature: Upper surface: Closest to N30A with 13A around tube opening. Lower surface: 21D.

*Upper petal.*—Margin: Entire, ruffled. Length from throat: Approximately 5.5 mm. Width: Approximately 5.8 mm.

*Lateral petals.*—Margin: Entire. Length from throat: approximately 4.2 mm. Width: Approximately 2.8 mm.

*Lower petal.*—Margin: Entire, ruffled. Length from throat: Approximately 3.6 mm. Width: Approximately 4.2 mm.

*Corolla tube.*—Length: Approximately 1.1 cm. Diameter at tube opening: Approximately 1.4 mm. Diameter at base: Approximately 1.1 mm. Texture of outer surface: Densely covered with short, soft hairs. Texture of inner surface: Glabrous except for hairs around tube opening. Color of outer surface: 6D. Color of inner surface: Closest to 6B.

*Calyx.*—Shape: Tubular, formed by 5 fused sepals. Length: Approximately 2.2 mm. Diameter: Approximately 1.5 mm. Sepal apex: Acute. Sepal width: 1 mm. Sepal texture: Outer/lower surface: Dense pubescence. Inner/upper: Glabrous. Sepal color: 145B.

*Reproductive organs.*—Stamen quantity: Four per flower, adnate to the corolla tube. Filament length: 0.7 mm. Filament color: 162A. Anther shape: 2 lobed, oblong. Anther length: 0.8 mm. Anther color: 200A. Amount of pollen: None observed. Pistil quantity: One per flower. Pistil length: 3.4 mm. Stigma shape: Cupped. Stigma length: 0.7 mm. Stigma color: 154C. Style length: Approximately 1.8 mm. Style color: 4C. Ovary length: 0.9 mm. Ovary color: 143C.

*Fruit.*—Classification: Drupe. Shape: Spherical. Diameter: 5 mm. Texture: Glabrous. Color of immature fruit: 144A. Color of mature fruit: Closest of N186B.

*Seed.*—Quantity: Sparse. Diameter: approximately 4 mm. Color: Closest to 200A.

Disease and pest resistance: Resistance to pathogens or pests common to *Lantana* has not been observed.

What is claimed is:

1. A new and distinct cultivar of *Lantana camara* plant named 'Balucrehot', substantially as herein shown and described.

* * * * *